United States Patent [19]

Maury

[11] 4,352,882
[45] Oct. 5, 1982

[54] PRODUCTION OF XANTHAN GUM BY EMULSION FERMENTATION

[75] Inventor: Lucien G. Maury, Wilmington, Del.

[73] Assignee: Kelco Biospecialties Limited, London, England

[21] Appl. No.: 299,709

[22] Filed: Sep. 8, 1981

[51] Int. Cl.³ .................. C12P 19/04; C12P 19/06
[52] U.S. Cl. ................................ 435/101; 435/104
[58] Field of Search ............... 435/101, 104, 248, 249

[56] References Cited

U.S. PATENT DOCUMENTS 3,455,786 7/1969 Miescher .............................. 435/104
3,723,255 3/1973 Walden ............................... 435/248
4,051,314 9/1977 Ohtsuka et al. ................. 435/101 X Primary Examiner—Lionel M. Shapiro
Attorney, Agent, or Firm—Gabriel Lopez; Hesna J. Pfeiffer

[57] ABSTRACT

Preparation of xanthan gum is effected by dispersing the aqueous xanthamonas culture medium in a water insoluble oil such as a hydrocarbon or vegetable oil. Such dispersions generate substantially less viscosity and as a result, fermentation can be carried out to a higher polymer content with less energy input.

4 Claims, No Drawings

PRODUCTION OF XANTHAN GUM BY EMULSION FERMENTATION

This invention relates to the production of polysaccharide gums by microbial fermentation. Specifically, it relates to a method of improving the yield of polysaccharide product which can be prepared by fermentation using either batch or continuous conditions.

Fermentations to produce a number of industrially important materials, such as antibiotics and fermentation polysaccharides such as xanthan gum, are usually carried out in aerated, deep vessels fitted with stirrer assemblies to provide effective mixing and aeration of the fermenting reaction mass. Aeration and mixing are required to assure air and nutrient exchange between the growing cells and the reaction medium. Inadequate aeration and mixing results in unacceptably low conversion efficiencies or cell death.

In polysaccharide fermentations, viscosity of the reaction mass increases with product formation since the product is soluble in the aqueous reaction medium. This viscosity increase reduces the efficiency of stirring and aeration and ultimately limits the amount of polymer which can be produced. Application of additional power to agitation is of some assistance, but this is also severely limited.

In the case of xanthan gum, 2.5 to 3% solutions with a viscosity of about 20,000 cps. are usually realized but it is very difficult to go much higher because the viscosity increases rapidly to a point where mixing and aeration become virtually impossible.

To improve aeration and stirring in viscous polysaccharide fermentations, it has been proposed to precipitate the gum as it is formed, thereby reducing the viscosity. This approach, however, can result in poisoning of the microorganism cells by the precipitant or in removal of them from the reaction mass with the gum. Moreover, removal of the precipitant from the product is usually necessary, which adds significantly to the cost of the process.

Now in accordance with this invention, it has been found that fermentations to produce polysaccharide gums can be carried to significantly higher gum concentrations if the aqueous culture medium is dispersed in a water immiscible oil which is a nonsolvent for the polysaccharide gum and the fermentation is effected within that dispersion. Expressly stated, the invention is an improvement in the method of conducting a fermentation reaction wherein an aqueous culture medium comprising a carbohydrate source and a nitrogen source is inoculated with a polysaccharide gum producing microorganism and said medium is mechanically agitated and aerated under conditions to effect fermentation thereof, the improvement which comprises said culture medium being dispersed in about 20 to 80% of its weight of a water insoluble oil in which the resultant polysaccharide is also insoluble. Preferred oil concentration is 40 to 80%.

Dispersing the reaction mixture in oil has two useful effects on the reaction. In addition to decreasing the viscosity of the reaction mixture as the concentration of polysaccharide therein increases, the oil significantly increases oxygen transfer efficiency leading to an increased rate of reaction. Thus, not only can a reaction be continued to a greater product concentration than has heretofore been found possible, it can arrive at that greater concentration in a time comparable to the time required to arrive at the heretofore maximum attainable concentration.

Substantially any water immiscible, water dispersible organic oil can be employed as the oil phase. Preferred oils are the higher boiling liquid hydrocarbons of the type having about 8 and more carbon atoms, boiling at about 100° C. and higher. These are usually supplied in complex mixtures such as paraffin oil, mineral oil, odorless mineral spirits, deodorized kerosene, or narrow boiling aliphatic hydrocarbons, although pure hydrocarbons such as n-octane per se will work equally well. Vegetable oils such as corn oil, peanut oil, soybean oil and safflower oil can also be used. Certain halogenated hydrocarbons have also been found useful.

The amount of oil to be used can vary from about 20 to about 70% of the total weight of the reaction mixture. As the concentration of oil in the mixture is increased, the productivity (grams of product per 100 ml. of reaction mix) of the process in a fixed time period increases significantly but at the same time, the viscosity of the reaction mix decreases. Thus, the viscosity of a reaction mix having more than 4% polysaccharide can be made substantially less than that of a totally aqueous mix having less than 3% simply by carrying out the reaction in the presence of a hydrocarbon oil. By currently known and used fermentation technology, a yield of 4% or even 3% would be virtually unattainable. The viscosity of such a reaction mix without the assistance of the oil, would be so great as virtually to prohibit agitation and efficient aeration of the mass.

Dispersion and stabilization of the aqueous phase of the reaction mass in the oil phase are further aided by the presence of an emulsifier. Preferred are nonionic emulsifiers of HLB ranging from about 12 to about 18. Typical of such emulsifiers are the ethoxylated fatty acids and ethoxylated glycerol, glycol and sorbitol fatty acid esters.

The method of the invention is applicable to both batch and continuous fermentations. In a conventional batch fermentation, the reaction is carried out for a period of about 36 to 48 hours until late log phase growth is achieved at which point the reaction mass is too viscous for further agitation. Normally, the reaction is stopped and the product recovered at this point. In carrying out the improved process, when late log phase growth is attained, the reaction is interrupted and about 1.2 to 1.5 volumes of the water insoluble oil are added along with additional sugar and nutrients. Growth is then allowed to continue until additional nutrients are consumed and/or yields of polysaccharide are at maximum.

The *Xanthomonas campestris* microorganism employed in the following examples was maintained on agar slants containing 2% agar, 2% glucose, 1% yeast extract and 1% tryptone. Slants were incubated at 30° C. for 24 hours or until profuse growth was obtained then refrigerated at 4° C. until used. Inoculum for the fermentations of the examples were prepared by inoculating with a loop from slant into 10 ml. of tryptone-glucose-yeast (TGY) broth contained in dimpled 125 ml. Erlenmeyer flasks and swirling these on a reciprocal shaker for 24 hours at 30° C. Five (5) ml. of this highly viscous culture was aseptically transferred to 50 ml. of the TGY broth in a 500 ml. Erlenmyer flask, followed again by swirling at 30° C. for 24 hours. This culture was then used to inoculate 300 ml. of broth in a 2 liter Erlenmeyer flask, which in turn was employed for fermentations carried out on the 14 liter scale.

EXAMPLE 1

The following materials were weighed into a beaker along with two liters of tap water:

yeast extract: 44 grams
dibasic ammonium phosphate: 11 grams
dibasic potassium phosphate: 11 grams
magnesium sulfate: 1.1 grams After stirring to dissolve the pH was adjusted to 7.0. This solution was charged to a 14 liter fermenter jar. Eight liters of additional water was added; the head plate and accessory equipment were installed; and the fermenter and contents were sterilized at 120° C. for 15 minutes. At the same time, a solution of 375 grams of glucose monohydrate was prepared in 500 ml. tap water and its pH was adjusted to 3 by the addition of several drops of hydrochloric acid. This was transferred to a 2 liter flask and sealed. The solution was sterilized by heating at 120° C. for 15 minutes.

The two 300 ml. growth cultures prepared as above were added to the sterilized solution in the fermenter. At the same time, the glucose solution was also added. Both solutions were added by means of a peristaltic pump to prevent contamination. Fermentation was allowed to proceed for 48 hours with agitation at about 800 rpm. At the end of the first 48 hours, 5 liters of the reaction mass was drawn off and 4 liters of sterile mineral oil added, in two, 2 liter increments. An additional 188 grams of the cellulose monohydrate in 250 ml. of water and 22 grams of yeast extract in 50 ml. of water was also added. The mixture was then stirred at 800 rpm for an additional 72 hours.

At the end of this run the reaction mass had a viscosity of approximately 3200 cps. measured with the Brookfield viscosimeter using number 3 spindle at 30 rpm and the total fermentation yield was about 4.1 grams per 100 ml., including the material which was tapped off at the end of 48 hours. By contrast, a 4% aqueous solution of xanthan gum alone has a viscosity of about 10,000 cps.

EXAMPLE 2

The procedure of Example 1 was repeated. After the initial 48 hour fermentation, the fermenter was tapped to a volume of 3 liters and a solution of 188 grams of addition glucose and 500 ml. of water plus, 100 ml. of water containing 22 grams of yeast extract was added. At the same time, 4 liters of sterilized deodorized kerosene was slowly added while stirring at 400 rpm. After another two days of fermentation another increment of 188 grams of the glucose in 500 ml. of water and another increment of the yeast extract, 22 grams in 100 ml. of water and one more liter of the deodorized kerosene was added. The stirring was continued then for another 24 hour period. The total polymer yield in this run was 5.2 grams per 100 ml. and the viscosity of the reaction mass was 10,800 cps. The viscosity of a 5.2% solution of xanthan in water would be expected to be about 40,000 cps.

EXAMPLE 3

To demonstrate the utility of the invention with other nonpolar water immiscible oils a series of fermentations were run in the presence of different oils.

Standard 50 ml. shake cultures of TGY broth were made up each containing 10 ml. of a selected oil. Each was inoculated with 5 ml. of a 24 hour shake culture of *Xanthomonas campestris*, then placed on a shaker and incubated at 30° C. for 48 hours. At the end of the 48 hours, viscosity of the reaction medium and the yield of polymer in each fermentation were determined. Data are recorded in the following Table I.

TABLE I

| Ex # | Oil | Viscosity* | Yield |
|---|---|---|---|
| Blank | None | 90 cps. | 0.38 g/100 ml. |
| 3a | Safflower | 140 cps. | 0.53 g/100 ml. |
| 3b | Soy | 140 cps. | 0.62 g/100 ml. |
| 3c | Corn | 120 cps. | 0.66 g/100 ml. |
| 3d | Peanut | 120 cps. | 0.67 g/100 ml. |
| 3e | Mineral | 292 cps. | 0.69 g/100 ml. |
| 3f | Silicone | 264 cps. | 0.73 g/100 ml. |

*Brookfield Viscometer - 30 RPM - #3 spindle.

EXAMPLE 4

Further standard 100 ml. shake flask cultures of *Xanthomonas campestris* were prepared and each was used to inoculate 2 liter shake flasks containing 25 ml. of a 5% sucrose solution and 2 grams of a yeast dispersion and varying amounts of the deodorized kerosene. These flasks were placed in an incubator reciprocating shaker at 30° C. and allowed to incubate for 48 hours. Dispersion viscosities and yields were then measured. Results are recorded in Table II below.

TABLE II

| Ex # | Amt. of Kerosene | % of Mixture | Viscosity* | Yield |
|---|---|---|---|---|
| Blank | none | — | 5,000 cps. | 0.84 g/100 ml. |
| 4a | 150 ml. | 50 | 38,000 cps. | 2.30 g/100 ml. |
| 4b | 200 ml. | 62 | 25,000 cps. | 3.68 g/100 ml. |
| 4c | 250 ml. | 68 | 12,000 cps. | 4.69 g/100 ml. |

*Brookfield LVF viscometer - 6 RPM - #3 spindle.

What I claim and desire to protect under Letter of Patent is:

1. In the method of conducting a fermentation reaction wherein an aqueous culture medium comprising a carbohydrate source and a nitrogen source is inoculated with a polysaccharide gum producing microorganism and said medium is mechanically agitated and aerated under conditions to effect fermentation thereof, the improvement which comprises said culture medium being dispersed in about 20 to 80% of its weight of a water insoluble oil in which the resultant polysaccharide is also insoluble.

2. The method of claim 1 wherein the culture medium is dispersed in the oil via a surfactant.

3. The method of claim 1 wherein the water insoluble oil is a hydrocarbon having 8 or more carbon atoms or a mixture of such hydrocarbons.

4. The method of claim 1 wherein the water insoluble oil is mineral oil.

* * * * *

Disclaimer

4,352,882.—*Lucien G. Maury*, Wilmington, Del. PRODUCTION OF XANTHAN GUM BY EMULSION FERMENTATION. Patent dated Oct. 5, 1982. Disclaimer filed Dec. 18, 1985, by the assignee, *Kelco Biospecialties Ltd.*

Hereby enters this disclaimer to claim 2 of said patent.
[*Official Gazette March 11, 1986.*]